(12) United States Patent
Head

(10) Patent No.: US 11,819,695 B2
(45) Date of Patent: Nov. 21, 2023

(54) SYSTEM AND METHOD FOR INCREASING LEFT VENTRICULAR TORSION BY MULTI-POINT PACING

(71) Applicant: Douglas S. Head, Murrells Inlet, SC (US)

(72) Inventor: Douglas S. Head, Murrells Inlet, SC (US)

(*) Notice: Subject to any disclaimer, the term of this patent is extended or adjusted under 35 U.S.C. 154(b) by 93 days.

(21) Appl. No.: 16/952,683

(22) Filed: Nov. 19, 2020

(65) Prior Publication Data
US 2022/0152390 A1 May 19, 2022

(51) Int. Cl.
*A61N 1/362* (2006.01)
*A61N 1/368* (2006.01)
*A61N 1/05* (2006.01)

(52) U.S. Cl.
CPC ......... *A61N 1/3627* (2013.01); *A61N 1/0597* (2013.01); *A61N 1/368* (2013.01); *A61N 1/36842* (2017.08)

(58) Field of Classification Search
None
See application file for complete search history.

(56) References Cited

U.S. PATENT DOCUMENTS

| | | | |
|---|---|---|---|
| 8,075,471 B2 | 12/2011 | Trumble | |
| 2003/0149456 A1* | 8/2003 | Rottenberg | A61N 1/3752 607/37 |
| 2009/0030469 A1* | 1/2009 | Meiry | A61N 1/372 607/9 |
| 2019/0366098 A1* | 12/2019 | Bockeria | A61N 1/37205 |
| 2021/0128000 A1* | 5/2021 | Kheradvar | A61B 5/002 |

OTHER PUBLICATIONS

Center for Disease Control and Prevention. Heart Failure. Dec. 9, 2019. 3 pages https://www.cdc.gov/heartdisease/heart_failure.htm.
W. T. Abraham et al., A Randomized Controlled Trial to Evaluate the Safety and Efficacy of Cardiac Contractility Modulation; JACC: Heart Failure; 2018; vol. 6-No. 10; pp. 874-883.
E. Soohoo et al., Torsional Ventricular-Assist Device: Design Considerations and Prototype Development, ASME. Journal of Medical Devices; vol. 10; Jun. 2016; 2 pages.
E. Soohoo et al., Computational Studies on the Effects of Applied Apical Torsion for Cardiac Assist for Regional Wall Mechanics; IEEE Transactions On Biomedical Engineering; vol. 67-No. 7; 2020; 12 pages.
A. M. S. Omar et al., Left Ventricular Twist and Torsion: Research Observations and Clinical Applications; Circ Cardiovascular Imaging; vol. 8-No. 6; 2015; pp. 74-82.

(Continued)

*Primary Examiner* — Michael W Kahelin
(74) *Attorney, Agent, or Firm* — Dority & Manning, P.A.

(57) ABSTRACT

A method for increasing left ventricular torsion by multi-point pacing includes fitting a plurality of pacemaker points at an epicardium of a heart such that the plurality of pacemaker points are positioned proximate an apex of a left ventricular muscle of the heart and sequentially pacing the plurality of pacemaker points. The left ventricular muscle of the heart twists in response to the sequential pacing. A system for implementing multi-point ventricular pacing is also provided.

15 Claims, 3 Drawing Sheets

(56) References Cited

OTHER PUBLICATIONS

S. Nakatani, Left Ventricular Rotation and Twist: Why Should We Learn ?; Journal of Cardiovascular Ultrasound; vol. 19(1); Mar. 2011; pp. 1-6.
E. J. Stöhr et al., Left ventricular twist mechanics in the context of normal physiology and cardiovascular disease: a review of studies using speckle tracking echocardiography; American Physiological Society; vol. 311-Issue 3; Sep. 2016; pp. H633-H644.
S. Toumanidis et al., Atrioventricular Left Ventricular Apical Pacing Improves Haemodynamic, Rotational, and Deformation Variables in Comparison to Pacing at the Lateral Wall in Intact Myocardium: Experimental Study; Cardiology Research and Practice; vol. 2014; Article ID 316290; 9 pages.

\* cited by examiner

SYSTEM AND METHOD FOR INCREASING LEFT VENTRICULAR TORSION BY MULTI-POINT PACING

FIELD OF THE INVENTION

The present disclosure is directed generally to ventricular pacemaker therapy in patients with heart failure with reduced ejection fraction.

BACKGROUND

Congestive heart failure is a leading healthcare problem in the United States (US). Moreover, the risk of congestive heart failure is increasing in the US as a result of population aging. In 2019, the Center for Disease Control and Prevention reported that six and a half (6.5) million adults in the US had congestive heart failure. Congestive heart failure cost the US an estimated thirty billion, seven hundred million dollars ($30.7 billion) in 2012.

To date, medical therapy has improved the treatment of heart failure with reduced ejection fraction, but certain patients continue to have symptoms despite treatment with known medical therapy. Cardiac resynchronization therapy by biventricular pacing and cardiac contractility modulation are the only available pacemaker therapies for treatment of heart failure with reduced ejection fraction. Certain patients suffering from heart failure with reduced ejection fraction do not meet the criteria for cardiac resynchronization therapy, and other patients do not improve after cardiac resynchronization therapy.

Known torsional ventricular assist devices mechanically generate torsion. In particular, the devices include a cup and an actuator. The cup touches the apical myocardium, and the actuator can rotate the cup. Operation of the device can create torsion, but direct mechanical contact and torsion can lead to undesirable cardiac contusion.

In view of the above, a need exists for an improved system and method for pacemaker therapy for heart failure with reduced ejection fraction.

SUMMARY

Aspects and advantages of the invention will be set forth in part in the following description, or may be apparent from the description, or may be learned through practice of the invention.

In general, the present disclosure is directed to systems and methods for rotational multi-point ventricular pacing, e.g., to increase left ventricular torsion in patients with heart failure with reduced ejection fraction.

In one example embodiment, for instance, the present disclosure is directed to a method for increasing left ventricular torsion by multi-point pacing. The method may include fitting a plurality of pacemaker points at the epicardium of a heart such that the plurality of pacemaker points are positioned proximate an apex of a left ventricular muscle of the heart and sequentially pacing the plurality of pacemaker points. The left ventricular muscle of the heart twists in response to the sequential pacing.

In a first example aspect, the method may further include implanting a pacemaker. In such example aspect, sequentially pacing the plurality of pacemaker points may include sequentially pacing the plurality of pacemaker points with the pacemaker. As an example, the pacemaker may be a dual chamber pacemaker.

In a second example aspect, the pacemaker may be implanted in a subclavicular area, such as the left subclavicular area. In such example aspect, the method may further include placing a transvenous atrial lead in a right atrial appendage.

In a third example aspect and as an alternative to the second example aspect, the pacemaker may be implanted in an abdominal wall. In such example aspect, the method may further include placing an epicardial atrial lead.

In a fourth example aspect, the plurality of pacemaker points are mounted on a strip and form a multi-point epicardial strip. In such example aspect, the method may further include connecting the multi-point epicardial strip to a ventricular header of a pacemaker.

In a fifth example aspect, the plurality of pacemaker points may be connected to a junction box. In such example aspect, the method may further include connecting the junction box to a ventricular header of a pacemaker.

In a sixth example aspect and as an alternative to the fifth example aspect, the method may include connecting each of the plurality of pacemaker points to a respective ventricular header of a pacemaker.

In a seventh example aspect, fitting the plurality of pacemaker points may include fitting the plurality of pacemaker points such that the plurality of pacemaker points are proximate the apex of the left ventricular muscle of the heart with a counterclockwise distribution and a superior angulation. In such example aspect, sequentially pacing the plurality of pacemaker points may include sequentially pacing the plurality of pacemaker points in order of the counterclockwise distribution of the plurality of pacemaker points.

In an eighth example aspect, during the sequential pacing of the plurality of pacemaker points, the plurality of pacemaker points may be paced no less than one millisecond and no more than ten milliseconds apart.

In a ninth example aspect, the plurality of pacemaker points may include no less than three pacemaker points and no more than seven pacemaker points.

In another example embodiment, for instance, the present disclosure is directed to a system for increasing left ventricular torsion by multi-point pacing. The system may include a strip. A plurality of pacemaker points may be positioned on the strip such that the plurality of pacemaker points are linearly distributed on the strip. The plurality of pacemaker points may include no less than two pacemaker points and no more than seven pacemaker points. The plurality of pacemaker points may be configured to fitted at an epicardium of a heart proximate an apex of a left ventricular muscle of the heart, and the plurality of pacemaker points may be configured to sequentially pace.

In yet another example embodiment, for instance, the present disclosure is directed to a system for increasing left ventricular torsion by multi-point pacing. The system may include a junction box. A plurality of pacemaker points may be electrically connected to the junction box. The plurality of pacemaker points may include no less than two pacemaker points and no more than seven pacemaker points. The plurality of pacemaker points may be configured to fitted at an epicardium of a heart proximate an apex of a left ventricular muscle of the heart, the plurality of pacemaker points may be electrically connected to the junction box such that each of the plurality of pacemaker points paces in response to a respective electrical signal from the junction box, and the plurality of pacemaker points may be configured to sequentially pace.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures.

DETAILED DESCRIPTION

Figure 1:
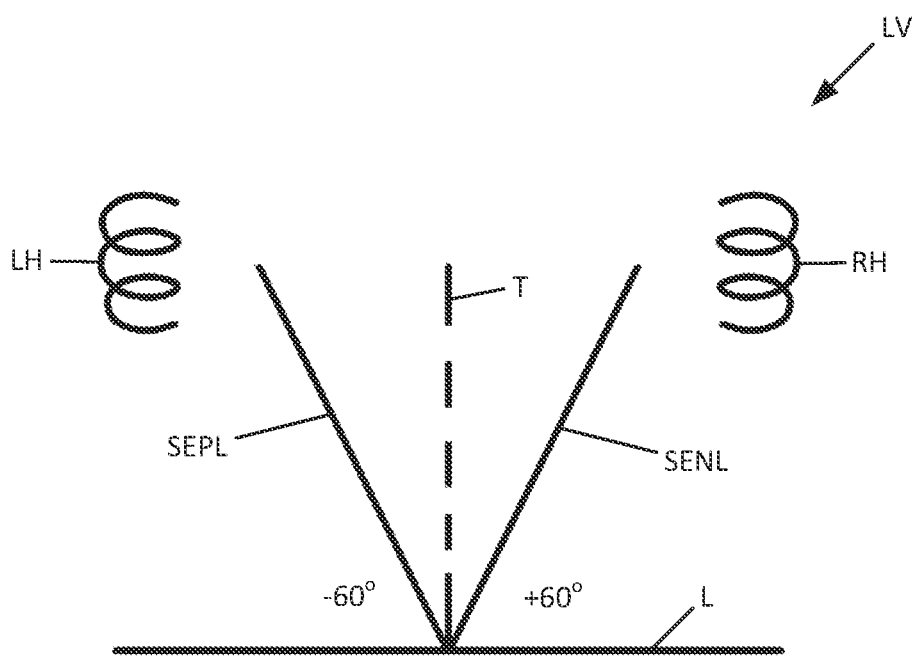
FIG. 1 is a schematic view of a human left ventricular muscle band.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

The present disclosure is generally directed to systems and methods for rotational multi-point ventricular pacing, e.g., to increase left ventricular torsion in patients with heart failure with reduced ejection fraction. For instance, sequential electrical pacing along multiple sites, e.g., starting near an apex, may be used to create twisting motion of a left ventricular muscle band.

The physiology of the human heart and the terminology used to describe the human heart are well known and not described in great detail herein for the sake of brevity. Nevertheless, a brief description of particularly relevant components of the human heart is provided below.

The left ventricle chamber of the human heart is one of four hollow chambers within the heart. Moreover, the left ventricle chamber is one of the two lowers chambers of the human heart. The left ventricle chamber is positioned on a left-hand side between the left atrium and the aorta. The left ventricle chamber is separated from the left atrium chamber by the mitral valve, and the left ventricle chamber is separated from the aorta by the aortic valve.

The left ventricle chamber is formed within the left ventricular muscle band, and the left ventricular muscle band may contract to pump blood. For instance, during normal operation, oxygenated blood continuously passes down from the left atrium into the left ventricle via the mitral valve due to contractions of the left ventricular muscle band. The oxygenated blood in the left ventricle then passes through the aortic valve and aortic arch before being carried to other organs.

FIG. 1 is a schematic view of a human left ventricular muscle band LV. As noted above, the left ventricular muscle band LV may contact to pump blood in the left ventricle chamber. The left ventricular muscle band LV includes two muscular helixes that surround the mid-ventricular circumferential layer of muscle fibers, namely, subendocardial fibers SENL and subepicardial fibers SEPL. As shown in FIG. 1, a layer of subendocardial muscle fibers SENL runs or extends at an angle of approximately positive sixty degrees (60°) to a long axis L in a right-hand helix RH. Conversely, a layer of subepicardial muscle fibers SEPL runs or extends at an angle approximately negative sixty degrees (−60°) from the long axis L in a left-hand helix LH. The layer of subepicardial muscle fibers SEPL is positioned over or outward of the layer of subendocardial muscle fibers SENL.

Figure 2:
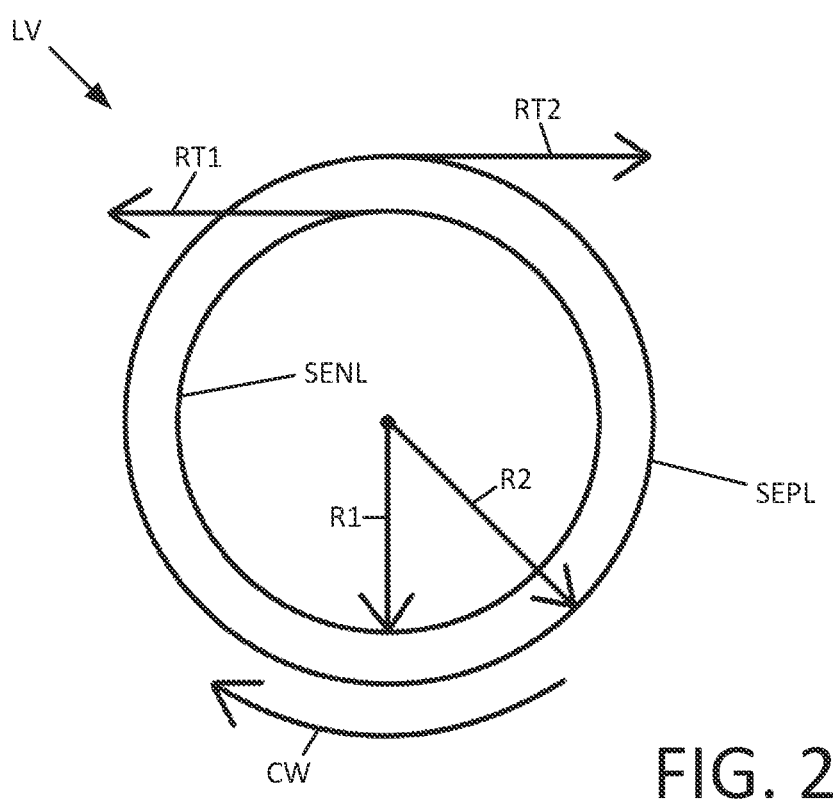
FIG. 2 is a schematic view of a base of the human left ventricular muscle band.
Figure 3:
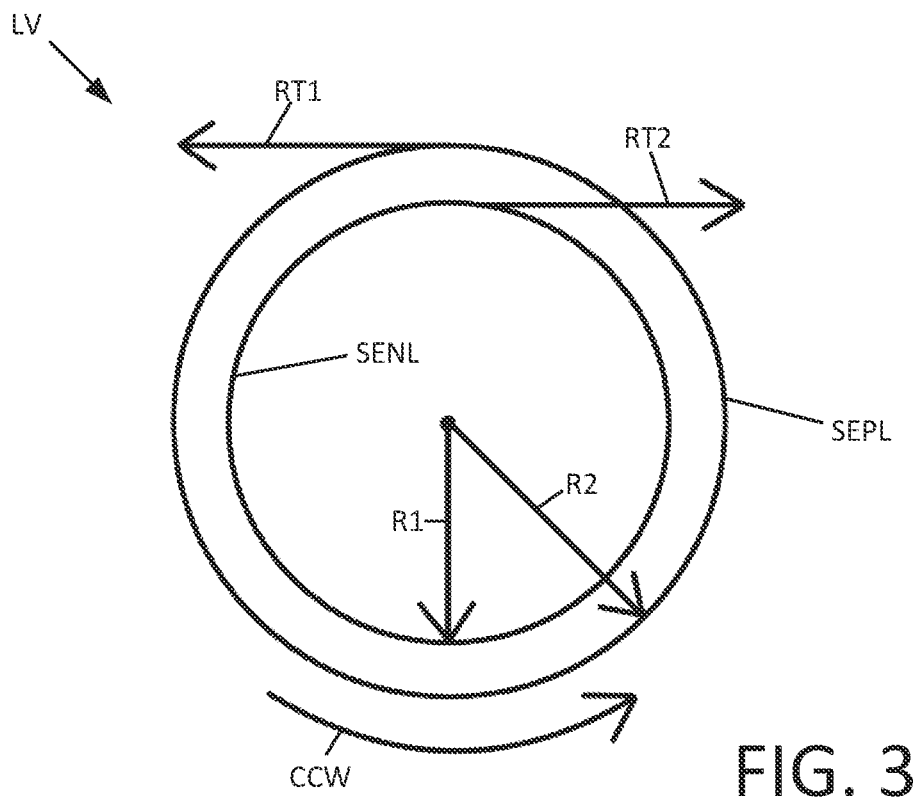
FIG. 3 is a schematic view of an apex of the human left ventricular muscle band.

FIG. 2 is a schematic view of a base B of left ventricular muscle band LV and the subendocardial fibers SENL and subepicardial fibers SEPL at the base B. FIG. 3 is a schematic view of an apex A of left ventricular muscle band LV and the subendocardial fibers SENL and subepicardial fibers SEPL at the apex A. As shown in FIGS. 2 and 3, during contractions of the left ventricular muscle band LV, the subepicardial muscle fibers SEPL rotate the base B of the left ventricular muscle band LV in a clockwise direction CW and the apex A in a counterclockwise direction CCW (e.g., according to the right-hand rule). Conversely, the subendocardial muscle fibers SENL rotate the base B of the left ventricular muscle band LV in a counterclockwise direction CCW and the apex A in a clockwise direction CW (e.g., according to the right-hand rule). Thus, the subepicardial muscle fibers SEPL may rotate the apex A and base B in opposite directions relative to the subendocardial muscle fibers SENL.

Due to the opposite rotational directions provided by contractions of the subendocardial fibers SENL and subepicardial fibers SEPL, the left ventricular muscle band LV may twist during contractions. Without wishing to be bound by theory, such twisting may reduce transmural stress of the left ventricular muscle band LV. Moreover, the subepicardial muscle fibers SEPL may provide more torque than the subendocardial fibers SENL, e.g., due to being positioned outward of the subendocardial fibers SENL. For instance, the subepicardial muscle fibers SEPL may be positioned a radial distance R2 from a center of the left ventricular, and the subendocardial fibers SENL may be positioned a radial distance R1 from a center of the left ventricular, with the radial distance R2 being greater than the radial distance R1. Thus, rotation of the subepicardial muscle fibers SEPL may predominate over rotation of the subendocardial fibers SENL, e.g., such that overall rotation of the apex A is greater than the base B, during contraction of the left ventricular muscle band LV due to a rotational torque RT2 of the subepicardial muscle fibers SEPL being greater than a rotational torque RT1 of the subendocardial fibers SENL.

In patients with heart failure with reduced ejection fraction, apical rotation of the left ventricular muscle band LV and overall systolic twist of the left ventricular muscle band LV are reduced. A magnitude of such reductions may be proportional to a degree of ejection fraction impairment of the left ventricular muscle band LV. As the left ventricle chamber becomes rounded as a result of heart failure with reduced ejection fraction, the angles of the subendocardial fibers SENL and/or subepicardial fibers SEPL from the long axis L (e.g., shown in FIG. 1) may increase. The increasing angle may cause the subendocardial fibers SENL and/or subepicardial fibers SEPL to run or extend more in a transverse direction T, e.g., that is perpendicular to the long axis L. Such reorientation of the subendocardial fibers SENL and/or subepicardial fibers SEPL may reduce rotation or twist of the left ventricular muscle band LV thereby reducing blood flow through the left ventricular.

As discussed in greater detail below, the present disclosure provides systems and methods for rotational multi-point ventricular pacing, e.g., to increase left ventricular torsion in patients with heart failure with reduced ejection fraction. For instance, sequential electrical pacing along multiple sites, e.g., starting near the apex A, may be used to create twisting motion of the left ventricular muscle band LV. Thus, the systems and methods of the present disclosure may advantageously assist with treating patients with heart failure with reduced ejection fraction.

Figure 4:
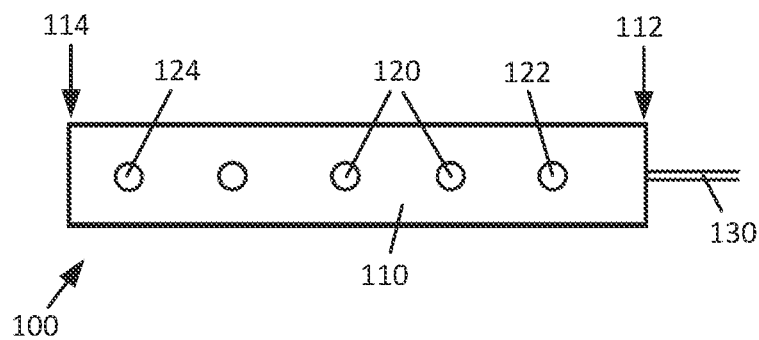
FIG. 4 is a plan view of a multi-point epicardial strip according to an example embodiment of the present subject matter.

FIG. 4 is a plan view of a multi-point epicardial strip 100 according to an example embodiment of the present subject matter. As shown in FIG. 4, multi-point epicardial strip 100 includes a strip 110 and a plurality of pacemaker points 120. Pacemaker points 120 may be positioned on strip 110. Thus, strip 110 may be a mounting structure for pacemaker points 120. Moreover, the relative positioning of pacemaker points 120 on strip 110 may be fixed due to pacemaker points 120 being mounted to strip 110.

Strip 110 may be constructed of a biocompatible material. For instance, strip 110 may be constructed of or with a plastic, such as cyclic olefin copolymer (COC), polycarbonate (PC), polyetherimide (PEI), medical grade polyvinylchloride (PVC), polyethersulfone (PES), polyethylene (PE), polyetheretherketone (PEEK), polypropylene (PP), etc. Thus, strip 110 may be disposed on or proximate the left ventricular muscle band LV, e.g., the subepicardial muscle fibers SEPL, without an adverse reaction or with a suitably limited adverse reaction. Strip 110 may also be deformable such that strip 110 may be shaped to fit onto or proximate the left ventricular muscle band LV, e.g., the subepicardial muscle fibers SEPL. Thus, strip 110 may be constructed of or with a deformable material, such as one or more of the above recited plastics, to allow strip 110 to be shaped to complement the shape of the left ventricular muscle band LV, e.g., the subepicardial muscle fibers SEPL. Moreover, as discussed in greater detail below, strip 110 may be deformed to position pacemaker points 120 at suitable locations on or proximate the left ventricular muscle band LV, e.g., the subepicardial muscle fibers SEPL.

Strip 110 may be elongated between a first end portion 112 and a second end portion 114. Strip 110 may have a length between first and second end portions 112, 114. The length of strip 110 may be selected such that strip 110 fits onto or proximate the left ventricular muscle band LV, e.g., the subepicardial muscle fibers SEPL, while providing a suitable distribution of pacemaker points 120 on strip 110. For instance, pacemaker points 120 may be linearly distributed on strip 110 between first and second end portions 112, 114. Moreover, pacemaker points 120 may be spaced apart on strip 110 between first and second end portions 112, 114. For instance, pacemaker points 120 may be uniformly spaced apart on strip 110 between first and second end portions 112, 114. By spacing pacemaker points 120 on strip 110, each pacemaker point 120 may pace a respective region of the left ventricular muscle band LV, e.g., the subepicardial muscle fibers SEPL, as discussed in greater detail below. As an example, the length of strip 110 may be, e.g., no less than three and a half centimeters (3.5 cm) and no greater than twenty centimeters (20 cm). Such sizing of strip 110 may advantageously allow strip to be positioned onto or proximate the left ventricular muscle band LV, e.g., the subepicardial muscle fibers SEPL, while providing a suitable distribution of pacemaker points 120 on strip 110.

Figure 6:
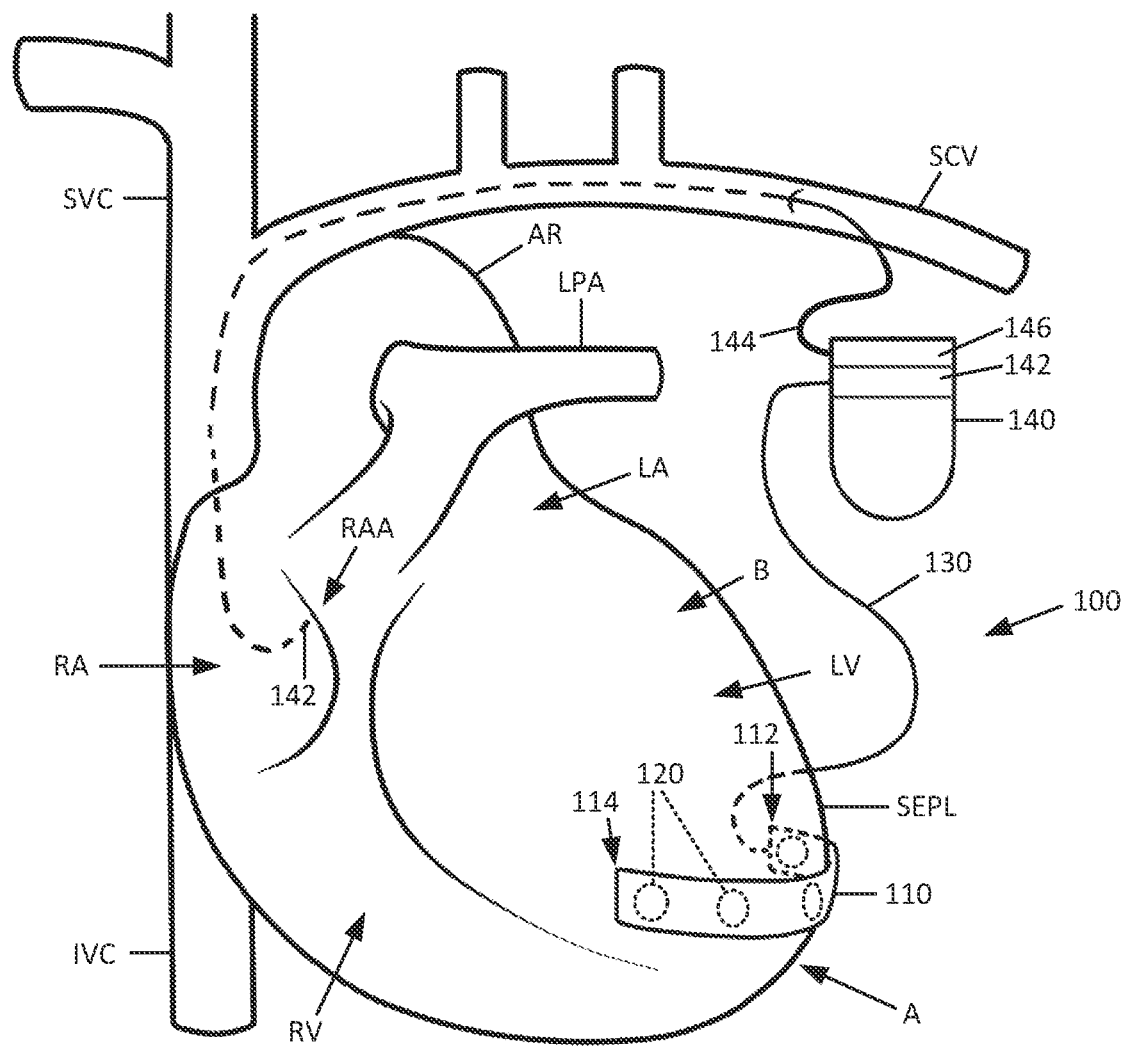
FIG. 6 is perspective view of the example multi-point epicardial strip of FIG. 4 fitted to a human heart.

Pacemaker points 120 are configured to be positioned on the left ventricular muscle band LV, e.g., the subepicardial muscle fibers SEPL. For instance, pacemaker points 120 may contact the left ventricular muscle band LV, e.g., the subepicardial muscle fibers SEPL. Pacemaker points 120 may electrically connected to a pacemaker, such as pacemaker 140 (FIG. 6). For instance, a wire 130 may extend from strip 110 and place pacemaker points 120 in electrical communication with the pacemaker, and the pacemaker may transmit electrical impulses to pacemaker points 120 via wire 130. In particular, the pacemaker may transmit the electrical impulses to pacemaker points 120 in order to stimulate the left ventricular muscle band LV, e.g., the subepicardial muscle fibers SEPL, and replace the defective natural pacemaker of the heart, the sinus node. Thus, pacemaker points 120 may be configured as electrodes for the pacemaker, and pacemaker points 120 may constructed of or with a biocompatible, electrically conductive material, such as platinum, nickel-cobalt alloy, titanium, etc.

Pacemaker points 120 may include no less than two (2) pacemaker points. Thus, epicardial strip 100 may be configured for multi-point pacing of the left ventricular muscle band LV, e.g., the subepicardial muscle fibers SEPL. In particular, epicardial strip 100 may be disposed on or proximate the left ventricular muscle band LV, e.g., the subepicardial muscle fibers SEPL, and the pacemaker may pace multiple (e.g., no less than two sites) on the left ventricular muscle band LV by transmitting the electrical impulses to pacemaker points 120. Pacemaker points 120 may include, e.g., two, three, four, five, six, seven, etc. pacemaker points, in certain example embodiments. For instance, pacemaker points 120 may include no more than seven (7) pacemaker points. Thus, e.g., pacemaker points 120 may include no less than two (2) pacemaker points and no more than seven (7) pacemaker points in certain example embodiments.

Figure 5:
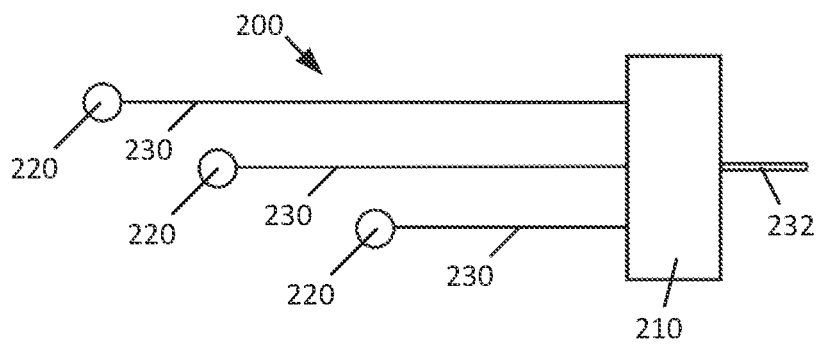
FIG. 5 is a schematic view of a plurality of epicardial leads according to an example embodiment of the present subject matter.

FIG. 5 is a plan view of multi-point epicardial leads 200 according to another example embodiment of the present subject matter. As shown in FIG. 5, multi-point epicardial leads 200 includes a junction box 210 and a plurality of pacemaker points 220. In contrast to multi-point epicardial strip 100, pacemaker points 220 are not positioned or mounted to a strip. Thus, the relative positioning of pacemaker points 220 is more flexible as compared to mounting pacemaker points 120 to strip 110 (FIG. 4). For instance, the relative positioning of pacemaker points 220 is not fixed due to a strip in multi-point epicardial leads 200.

Pacemaker points 220 are configured to be positioned on the left ventricular muscle band LV, e.g., the subepicardial muscle fibers SEPL. For instance, pacemaker points 220 may contact the left ventricular muscle band LV, e.g., the subepicardial muscle fibers SEPL. Pacemaker points 220 may electrically connected to a pacemaker, such as pacemaker 140 (FIG. 6), via junction box 210. For instance, each pacemaker point 220 may be connected to junction box 210 via a respective one of a plurality of wires 230. In addition, a wire 232 may extend from junction box 210 to the pacemaker. Thus, junction box 210, wires 230, and wire 232 may place pacemaker points 220 in electrical communication with the pacemaker, and the pacemaker may transmit electrical impulses to pacemaker points 220 via junction box 210, wires 230, and wire 232. In particular, the pacemaker may transmit the electrical impulses to pacemaker points 220 in order to stimulate the left ventricular muscle band LV, e.g., the subepicardial muscle fibers SEPL, and replace the defective natural pacemaker of the heart, the sinus node. Thus, pacemaker points 220 may be configured as electrodes for the pacemaker, and pacemaker points 220 may constructed of or with a biocompatible, electrically conductive material, such as platinum, nickel-cobalt alloy, titanium, etc.

Pacemaker points 220 may include no less than two (2) pacemaker points. Thus, multi-point epicardial leads 200 may be configured for multi-point pacing of the left ventricular muscle band LV, e.g., the subepicardial muscle fibers SEPL. In particular, multi-point epicardial leads 200 may be disposed on or proximate the left ventricular muscle band LV, e.g., the subepicardial muscle fibers SEPL, and the pacemaker may pace multiple (e.g., no less than two sites) on the left ventricular muscle band LV by transmitting the electrical impulses to pacemaker points 220. Pacemaker points 220 may include, e.g., two, three, four, five, six, seven, etc. pacemaker points, in certain example embodiments. For instance, pacemaker points 220 may include no more than seven (7) pacemaker points. Thus, e.g., pacemaker points 220 may include no less than two (2) pacemaker points and no more than seven (7) pacemaker points in certain example embodiments.

FIG. 6 is perspective view of multi-point epicardial strip 100 of FIG. 4 fitted to a human heart. As may be seen in FIG. 6, multi-point epicardial strip 100 may be fitted on an epicardium, e.g., such that pacemaker points 120 are positioned proximate an apex A of a left ventricular muscle band LV of the heart. For instance, a surgeon may position strip 110 on the epicardium in order to quickly and/or precisely position pacemaker points 120 proximate apex A of the left ventricular muscle band LV of the heart. As an example, pacemaker points 120 may be proximate the apex A of the left ventricular muscle band LV with a counterclockwise distribution and a superior angulation. Moreover, a first point 122 (FIG. 4) of pacemaker points 120 may be positioned at first end portion 112 of strip 110, and a last point 124 (FIG. 4) of pacemaker points 120 may be positioned at second end portion 114 of strip 110. Pacemaker points 120 may be positioned proximate the apex A of the left ventricular muscle band LV with the counterclockwise distribution and the superior angulation from first end portion 112 of strip 110 to second end portion 114 of strip 110. Thus, pacemaker points 120 may have the counterclockwise distribution and the superior angulation from first point 122 to last point 124, or vice versa, in certain example embodiments.

As shown in FIG. 6, multi-point epicardial strip 100 may be connected to a pacemaker 140 via wire 130. For instance, multi-point epicardial strip 100 may be connected to a ventricular header 142 of pacemaker 140 via wire 130. Pacemaker 140 may be operable to sequentially pace pacemaker points 120, as described in greater detail below. Pacemaker 140 may be a dual chamber pacemaker in certain example embodiments.

It will be understood that the arrangement shown in FIG. 6 is provided by way of example only. In alternative example embodiments, multi-point epicardial leads 200 (FIG. 5) may be used in place of multi-point epicardial strip 100, e.g., with pacemaker points 220 arranged in a similar manner to that shown for pacemaker points 120 in FIG. 6. In such example embodiments, junction box 210 may be connected to ventricular header 142 of pacemaker 140 via wire 232. As another example, pacemaker points 220 of multi-point epicardial leads 200 may be directly connected to pacemaker 140, e.g., such that multi-point epicardial leads 200 does not include junction box 210. Moreover, each wire of wires 230 may be connected to a respective ventricular header 142 of pacemaker 140. In such example embodiments, a number of ventricular headers 142 of pacemaker 140 may correspond to (e.g., or be no less than) a number of pacemaker points 220.

Turning back to FIG. 6, a surgeon may implant pacemaker 140, e.g., in addition to fitting multi-point epicardial strip 100. For instance, pacemaker 140 may be implanted within a subclavicular area of a patient. For instance, as shown in FIG. 6, pacemaker 140 may be implanted within a left subclavicular area of the patient. However, in alternative example embodiments, pacemaker 140 may be implanted within a right subclavicular area of the patient. With pacemaker 140 positioned in the subclavicular area, a transvenous atrial lead 142 may be placed within a right atrial appendage RAA of the heart. A wire 144 may extend through a left subclavian vein SCV from transvenous atrial lead 142 in the right atrial appendage RAA to pacemaker 140, e.g., an atrial header 146 of the pacemaker 140. As an example alternative to the arrangement shown in FIG. 6, pacemaker 140 may be implanted within an abdominal wall below the heart, and an epicardial atrial lead may be placed on the heart.

In FIG. 6, various portions of the heart are indicated for convenience. In particular, a superior vena cava SVC, an inferior vena cava IVC, a left pulmonary artery LPA, an aorta AR, a left atrium LA, a right atrium RA, and a right ventricle RV are referenced in FIG. 6 for convenience and to aid one of skill in the art in understanding FIG. 6.

With multi-point epicardial strip 100 fitted as shown in FIG. 6, pacemaker points 120 may be sequentially paced, e.g., with pacemaker 140. As an example, pacemaker 140 may sequentially pace pacemaker points 120 in order of the counterclockwise distribution of pacemaker points 120. Thus, e.g., first point 122 (FIG. 4) of pacemaker points 120 at first end portion 112 of strip 110 may be paced first in the sequential pacing of pacemaker points 120, and last point 124 (FIG. 4) of pacemaker points 120 positioned at second end portion 114 of strip 110 may be paced last in the sequential pacing of pacemaker points 120. During the sequential pacing of pacemaker points 120, pacemaker points 120 may be paced no less than one millisecond (1 ms) and no more than ten milliseconds (10 ms) apart.

By utilizing multi-point epicardial strip 100 and/or multi-point epicardial leads 200, the left ventricular muscle band LV may be sequentially paced with pacemaker 140. Moreover, the left ventricular muscle band LV, e.g., proximate the apex A of the left ventricular muscle band LV, may twist in response to the sequential pacing with pacemaker 140. The twisting motion of the left ventricular muscle band LV may advantageously increase rotation of the left ventricular muscle band LV and thereby increase blood flow through the left ventricular LV, e.g., in patients with heart failure with reduced ejection fraction.

As may be seen from the above, sequential electrical pacing along multiple sites starting near the apex A may be used to create a twisting motion of the left ventricular muscle band LV. Moreover, such ventricular epicardial pacing may be achieved with multi-point epicardial strip 100 and/or multi-point epicardial leads 200. For instance, pacemaker points 120 and/or pacemaker points 220 may be placed near the apex A in a counterclockwise rotation and in a slight superior angulation. Sequentially, pacing starts at one end of the distributed pacemaker points 120 and/or pacemaker points 220, e.g., a first one of pacemaker points 120, then a second one of pacemaker points 120, then a third one of pacemaker points 120, then a fourth one of pacemaker points 120, then a fifth one of pacemaker points 120, etc. After the first one of pacemaker points 120, each of the other pacemaker points 120 may be paced sequentially, e.g., every one to ten milliseconds (1-10 ms) to produce rotation of the left ventricular muscle band LV at the apex A.

The present subject matter may be a combination of endovascular and epicardial pacing. The sequential pacing described herein may result in an improvement of ejection fraction and clinical status. Further, the present subject matter may be utilized independently, e.g., not in parallel with biventricular pacemaking, in patients suffering from heart failure with reduced ejection fraction.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed:

1. A method for increasing left ventricular torsion by multi-point pacing, comprising:
    fitting a plurality of pacemaker points at an epicardium of a heart such that the plurality of pacemaker points are positioned proximate an apex of a left ventricular muscle of the heart; and
    sequentially pacing the plurality of pacemaker points,
    wherein the left ventricular muscle of the heart twists in response to the sequential pacing, and
    wherein fitting the plurality of pacemaker points comprises fitting the plurality of pacemaker points such that the plurality of pacemaker points are proximate the apex of the left ventricular muscle of the heart with a counterclockwise distribution and a superior angulation.

2. The method of claim 1, further comprising implanting a pacemaker, and wherein sequentially pacing the plurality of pacemaker points comprises sequentially pacing the plurality of pacemaker points with the pacemaker.

3. The method of claim 2, wherein the pacemaker is a dual chamber pacemaker.

4. The method of claim 2, wherein the pacemaker is implanted in a subclavicular area.

5. The method of claim 4, further comprising placing a transvenous atrial lead in a right atrial appendage.

6. The method of claim 2, wherein the pacemaker is implanted in an abdominal wall.

7. The method of claim 6, further comprising placing an epicardial atrial lead.

8. The method of claim 1, wherein the plurality of pacemaker points are mounted on a strip and form a multi-point epicardial strip.

9. The method of claim 8, further comprising connecting the multi-point epicardial strip to a ventricular header of a pacemaker.

10. The method of claim 1, wherein the plurality of pacemaker points are connected to a junction box.

11. The method of claim 10, further comprising connecting the junction box to a ventricular header of a pacemaker.

12. The method of claim 1, further comprising connecting each of the plurality of pacemaker points to a respective ventricular header of a pacemaker.

13. The method of claim 1, wherein sequentially pacing the plurality of pacemaker points comprises sequentially pacing the plurality of pacemaker points in order of the counterclockwise distribution of the plurality of pacemaker points.

14. The method of claim 1, wherein, during the sequential pacing of the plurality of pacemaker points, the plurality of pacemaker points are paced no less than one millisecond and no more than ten milliseconds apart.

15. The method of claim 1, wherein the plurality of pacemaker points comprises no less than three pacemaker points and no more than seven pacemaker points.

* * * * *